US009993531B2

(12) United States Patent
Siegel et al.

(10) Patent No.: US 9,993,531 B2
(45) Date of Patent: *Jun. 12, 2018

(54) FORMULATION FOR ORAL ADMINISTRATION OF PROTEINS

(71) Applicant: ALVINE PHARMACEUTICALS, INC., San Carlos, CA (US)

(72) Inventors: Matthew J. Siegel, Menlo Park, CA (US); Bret Berner, Half Moon Bay, CA (US)

(73) Assignee: Immunogenics LLC, Newport Beach, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 15/045,111

(22) Filed: Feb. 16, 2016

(65) Prior Publication Data

US 2016/0235825 A1     Aug. 18, 2016

Related U.S. Application Data

(63) Continuation of application No. 14/634,503, filed on Feb. 27, 2015, now abandoned, which is a continuation of application No. 13/058,830, filed as application No. PCT/US2009/004791 on Aug. 21, 2009, now Pat. No. 8,980,254.

(60) Provisional application No. 61/090,831, filed on Aug. 21, 2008.

(51) Int. Cl.
*A61K 38/48* (2006.01)
*A61K 9/20* (2006.01)
*A61K 9/00* (2006.01)
*C12N 9/50* (2006.01)
*C12N 9/96* (2006.01)

(52) U.S. Cl.
CPC ........ *A61K 38/4873* (2013.01); *A61K 9/0053* (2013.01); *A61K 9/2009* (2013.01); *A61K 9/2013* (2013.01); *A61K 38/48* (2013.01); *C12N 9/50* (2013.01); *C12N 9/96* (2013.01); *C12Y 304/22* (2013.01)

(58) Field of Classification Search
CPC .......... A61K 9/2009; A61K 9/2013; A61K 38/4873; A61K 9/0053; A61K 38/48; C12N 9/50; C12N 9/96; C12Y 304/22
See application file for complete search history.

(56) References Cited

U.S. PATENT DOCUMENTS

| | | | |
|---|---|---|---|
| 4,477,434 A | 10/1984 | Kosaka | |
| 4,937,183 A | 6/1990 | Ultee et al. | |
| 5,466,547 A | 11/1995 | Khoe | |
| 6,291,533 B1 | 9/2001 | Fleischner | |
| 6,541,606 B2 | 4/2003 | Margolin et al. | |
| 6,562,339 B2 | 5/2003 | Eisenhardt et al. | |
| 6,660,313 B2 | 12/2003 | Kulkarni et al. | |
| 6,730,493 B1 | 5/2004 | Schwan-Jonczyk et al. | |
| 7,244,709 B2 | 7/2007 | Quay et al. | |
| 7,265,097 B2 | 9/2007 | Kydonieus et al. | |
| 7,291,598 B2 | 11/2007 | Sung et al. | |
| 7,303,871 B2 | 12/2007 | Hausch et al. | |
| 7,320,788 B2 | 1/2008 | Shan et al. | |
| 7,351,741 B2 | 4/2008 | Weidner et al. | |
| 2003/0007959 A1 | 1/2003 | Lezdey et al. | |
| 2003/0215438 A1 | 11/2003 | Hausch et al. | |
| 2004/0058870 A1 | 3/2004 | Froland et al. | |
| 2004/0248821 A1 | 12/2004 | Ziegler | |
| 2005/0249719 A1 | 11/2005 | Shan et al. | |
| 2006/0019941 A1 | 1/2006 | Adams et al. | |
| 2006/0083727 A1 | 4/2006 | Kajander et al. | |
| 2006/0134018 A1 | 6/2006 | Trivedi et al. | |
| 2007/0044906 A1 | 3/2007 | Park | |
| 2007/0047303 A1 | 3/2007 | Kim | |
| 2007/0140978 A1 | 6/2007 | Dillon et al. | |
| 2007/0197439 A1 | 8/2007 | Zhu et al. | |
| 2007/0243254 A1 | 10/2007 | Edgren et al. | |
| 2008/0115411 A1 | 5/2008 | Ramsey | |
| 2008/0115428 A1 | 5/2008 | Schlam et al. | |
| 2008/0125437 A1 | 5/2008 | Dong et al. | |
| 2008/0193436 A1 | 8/2008 | Shan et al. | |

FOREIGN PATENT DOCUMENTS

| | | |
|---|---|---|
| JP | 2008-503489 A | 2/2008 |
| JP | 2008-504249 A | 2/2008 |
| JP | 2008-515389 A | 5/2008 |
| WO | 1999041361 A1 | 8/1999 |
| WO | 2008115428 A2 | 9/2008 |

OTHER PUBLICATIONS

Ascenzi et al., "Inhibition of Cysteine Protease Activity by NO-donors", Current Protein and Peptide Science (2001), 2:137-153.
Bjorne et al., "Nitrite in saliva increases gastric mucosal blood flow and mucus thickness", The Journal of Clinical Investigation (2004), 113(1):106-114.
Venturini et al., "Nitric Oxide Inhibits Cruzipain, the Major Papain-like Cysteine Proteinase from Trypanosoma cruzi", Biochemical and Biophysical Research Communications (2000), 270:437-441.
Wang et al., "Identification of Amino Acids Important for the Catalytic Activity of the Collagen Glucosyltransferase Associated with the Multifunctional Lysyl Hydroxylase 3 (LH3)", The Journal of Biological Chemistry (2002), 277 (21):18568-18573.
Bethune et al., "Heterologous expression, purification, refolding, and structural-functional characterization of EP-B2, a self-activating barley cysteine endoprotease", Chem Bioi (Jun. 2006), 13(6):637-647.
Gass et al., "Combination enzyme therapy for gastric digestion of dietary gluten in patients with celiac sprue", Gastroenterology (Aug. 2007), 133(2):472-480.

(Continued)

*Primary Examiner* — Satyendra K Singh
(74) *Attorney, Agent, or Firm* — Pamela J. Sherwood; Bozicevic, Field & Francis LLP (57) ABSTRACT

Pharmaceutical formulations of orally administered proteins can be stabilized from oxidative degradation and inactivation in the stomach and GI tract by the addition of an antioxidant.

7 Claims, 8 Drawing Sheets

(56) References Cited

OTHER PUBLICATIONS

Siegel et al., "Rational design of combination enzyme therapy for celiac sprue", Chem Bioi (Jun. 2006), 13 (6):649-658.
Gass et al., Effect of Barley Endoprotease EP-82 on Gluten Digestion in the Intact Rat, The Journal of Pharmacology and Experimental Therapeutics, 2006, vol. 318, No. 3, pp. 1178-1186.
Manhart et al., Administration of proteolytic enzymes bromelain and trypsin diminish the number of CD4+ cells and the u interteron-c response in Peyer's patches and spleen in endotoxemic balb/c mice, Cellular Immunology, 2002, vol. 215, pp. 113-119.

FORMULATION FOR ORAL ADMINISTRATION OF PROTEINS

FIELD OF THE INVENTION

This invention relates to methods and compositions for stabilizing proteases intended for oral administration against degradation in the stomach and in gastric fluid and in other physiological fluids that may oxidize and degrade these proteins. The present invention therefore relates to the fields of biology, chemistry, molecular biology, medicinal chemistry, medicine, and pharmacology.

DESCRIPTION OF RELATED DISCLOSURES

Oral delivery of proteins to the gastrointestinal tract is known to be problematic, as a result of poor protein stability due to both gastric pH and proteolytic digestion by enzymes, as well as poor absorption. Many attempts have been made to deliver proteins by the oral route or locally to the stomach. U.S. Pat. Nos. 7,291,598; 7,265,097; and 7,244,709, for example, all use nanoparticles containing chitosan to improve the absorption and stability of proteins in the gastrointestinal (GI) tract. U.S. Pat. No. 6,541,606 utilizes crystalline proteins to avoid degradation in the stomach and for treatment of diseases of the GI tract and discusses potential bioadhesion to Peyer's patches to improve protein absorption from the GI tract. U.S. Pat. No. 7,351,741 describes additives to improve absorption of proteins from the GI tract. These patents describe the problems of stability of proteins in the GI tract due to acidic pH in the stomach and due to enzymatic digestion as well as poor absorption from the GI tract. The instability of proteins in the GI tract or stomach due to oxidation or non-proteolytic digestion is not described by any of the aforementioned references.

Lactase, a β-galactosidase that metabolizes lactose, and papain, a cysteine protease, are both enzymes administered orally as dietary supplements. Lactase is administered as a digestive aid for individuals that are deficient in the ability to digest lactose. For example, lactase from *Aspergillus oryzae* is administered as Lactaid® (Pleasantville, N.J.) as a dietary supplement, and U.S. Pat. Nos. 6,660,313 and 6,562,339 describe formulations of lactase for oral administration in dietary supplements. Papain, a cysteine protease, is administered as a digestive aid. However, its optimal temperature is 65° C., and it is not clear that papain is an active enzyme in the stomach.

U.S. Pat. Nos. 7,320,788 and 7,303,871 describe the use of glutenases, alone and in combination, as orally administered enzymes to digest gluten for treatment (and prevention of symptoms) of Celiac sprue. One of the enzymes described as a glutenase is a recombinant version of a cysteine endoprotease originally isolated from barley. In 1953, it was first recognized that ingestion of gluten, a common dietary protein present in wheat, barley and rye causes disease in sensitive individuals. Gluten is a complex mixture of glutamine- and proline-rich glutenin and prolamine molecules, which is thought to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of celiac sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations.

A related disease is dermatitis herpetiformis, which is a chronic eruption characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of dermatitis herpetiformis patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients. Dapsone, sulfapyridine and colchicines are sometimes prescribed for relief of itching due to dermatitis herpetiformis.

Celiac sprue and dermatitis herpetiformis are generally considered to be an autoimmune disease, and the antibodies found in the serum of the patients indicate an immunological basis of the disease. Antibodies to tissue transglutaminase (tTG) and gliadin appear in almost 100% of the patients with active Celiac sprue, and the presence of such antibodies, particularly of the IgA class, has been used in diagnosis of the disease.

The large majority of Celiac sprue and dermatitis herpetiformis patients express the HLA-DQ2 [DQ(a1*0501, b1*02)] and/or DQ8 [DQ(a1*0301, b1*0302)] molecules. It is believed that intestinal damage is caused by interactions between specific gliadin oligopeptides and HLA-DQ2 or DQ8, which in turn induce proliferation of T lymphocytes in the sub-epithelial layers. T helper 1 cells and cytokines apparently play a major role in a local inflammatory process leading to villus atrophy of the small intestine.

At the present time, the only treatment for Celiac sprue is the strict avoidance of all foods containing gluten, although clinical trials of glutenases are ongoing. While gluten withdrawal has transformed the prognosis for children diagnosed with Celiac sprue and substantially improved it for adult patients, some people still die of the disease, mainly adults who had severe disease at the outset. An important cause of death is lymphoreticular disease (especially intestinal lymphoma). It is not known whether a gluten-free diet diminishes this risk. Apparent clinical remission is often associated with histologic relapse that is detected only by review biopsies or by increased EMA titers.

Gluten is so widely used, for example in commercial soups, sauces, ice creams, hot dogs, and other foods, that patients need detailed lists of foodstuffs to avoid and expert advice from a dietitian familiar with Celiac sprue. Ingesting even small amounts of gluten may prevent remission or induce relapse. Supplementary vitamins, minerals, and hematinics may also be required, depending on the degree of deficiency experienced by a particular patient. A few patients respond poorly or not at all to gluten withdrawal, either because the diagnosis is incorrect or because the disease is refractory. In the latter case, oral corticosteroids (e.g., prednisone 10 to 20 mg bid) may induce response.

Perhaps the most promising new therapy in clinical development is the use of glutenases as described in U.S. Pat. Nos. 7,320,788 and 7,303,871 (incorporated herein by reference; see also PCT Pub. Nos. 2008/115428; 2008/115411; 2007/044906; and 2007/047303, each of which is incorporated herein by reference) to prevent and/or treat the symptoms of Celiac sprue and/or dermatitis herpetiformis by decreasing the levels of toxic gluten oligopeptides in foodstuffs, either prior to or after ingestion by a patient. These patent publications disclose that certain gluten oligopeptides are resistant to cleavage by gastric and pancreatic enzymes, that the presence of such peptides in the small intestine results in toxic effects in Celiac sprue (and dermatitis herpetiformis) patients, and that enzymatic treatment can remove such peptides and their toxic effects. By digestion with glutenases, these toxic oligopeptides are cleaved into fragments, thereby preventing or relieving their toxic effects in Celiac sprue or dermatitis herpetiformis patients.

Many glutenases comprise cysteine and/or methionine residues, and proteins containing cysteine or methionine can be subject to oxidation during storage either as bulk enzyme or as dosage forms, and enzymes with cysteine in the active site, specifically cysteine proteases, can be inactivated by oxidation of cysteine. The stability of these proteins during storage or after lyophilization may be improved by adding acetylcysteine or methionine to scavenge free radical attack.

A variety of antioxidants are known to be useful as preservatives during storage of pharmaceuticals and foods, including sulfur-containing antioxidants, free thiols, such as cysteine, homocysteine, thioglycerol, acetylcysteine, as well as sodium sulfite, sodium metabisulfite, sodium thiosulfate, and the like, disulfides (such as dithiothreitol and α-lipoic acid where free thiols can be generated), and other classes of antioxidants, such as chelating agents, such as EDTA, ascorbic acid, gallic acid and its derivatives, tocopherol and its derivatives, and others known in the art to prevent oxidation. Selection of an antioxidant that will work for a particular protein is often not predictable and involves trial and error.

Because prevention of oxidation in dosage forms involves limited volumes of drug, small amounts of antioxidant can be effective, because the concentration of the antioxidant in the dosage form is relatively large. However, the amount of antioxidant in the dosage form would have negligible activity in the larger volume of the stomach, which can be 1 liter in volume or more.

Certain cysteine proteases, in particular, papain and certain cathepsins, have been reported to be deactivated by S-nitrosylation of the active site cysteine (see Wang et al. (2000) JBC 2002 277(21):18568-73; Ascenzi et al. (2001) Curr. Protein Pept. Sci. 2: 137-153; and Venturini et al. (2000) Biochem. Biophys. Res. Commun. 270: 437-441.). Certain sulfhydryl containing NO donors have been demonstrated to reversibly inhibit this enzyme by S—NO bond formation at the active site, Cys25. This inhibition was reversed by dithiothreitol, but not by ascorbic acid. The researchers presumed that a disulfide bond between the papain and the S—NO donor was responsible for the inhibition.

Nitrate in saliva has been shown, in rats, to be converted to nitrite, which can then be further converted to NO at fasted gastric pH of 2 (Bjorne et al. (2004) J. Clin. Invest. 113: 106-114). Under such conditions, increased NO formation from nitrites and increased blood flow, presumably mediated by NO, were reportedly observed. It is known that, from the serosal side, nitric oxide acts on the stomach to influence gastrointestinal motility, possibly by forming S-nitrosyl thiol protein intermediates.

Thus, there remains a need for pharmaceutical formulations and unit dosage forms that can improve stability of a protein in the fed stomach. The present invention meets this and other needs.

SUMMARY OF THE INVENTION

In a first aspect, the present invention provides pharmaceutical formulations of a protein suitable for oral administration that stabilizes the protein in the fed stomach. In one embodiment, the protein is a protease. In one embodiment, the protease is a cysteine protease. In one embodiment, the formulation comprises, in addition to the protein, an antioxidant, such as a reducing agent and/or a chelating agent. In one embodiment, the antioxidant is a sulfur-containing antioxidant. In various embodiments, the sulfur containing antioxidant is a sulfate, a free thiol, or an agent that generates a free thiol in gastric fluid. In various embodiments, the sulfur containing antioxidant is selected from the group consisting of sodium sulfite, sodium metabisulfite, N-acetylcysteine, homocysteine, cysteine, monothioglycerol, sodium thiosulfate, α-lipoic acid, and dithiothreitol. In various embodiments, the pharmaceutical formulation optionally comprises a chelating agent. In one embodiment, the chelating agent is EDTA. In other embodiments, the chelating agent is citric acid.

In one embodiment of the first aspect of the invention, the protein is a cysteine protease capable of digesting a gluten peptide that is toxic to a Celiac sprue patient into non-toxic fragments, either alone or in combination with another protease. In one embodiment, the cysteine protease is barley endoprotease EPB2 or a modified form of that protease, or a recombinant version of either. In one embodiment, the barley endoprotease EPB2 is admixed with a prolyl endopeptidase (PEP). In one embodiment, the PEP is *Sphingomonas capsulata* PEP or a modified form of that protease, or a recombinant version of either. In one embodiment, the PEP is *Aspergillus niger* PEP or a modified form of that protease, or a recombinant version of either.

In a second aspect, the present invention provides a method for preventing and/or treating Celiac sprue and/or dermatitis herpetiformis in a patient, said method comprising the step of orally administering a stabilized cysteine protease containing pharmaceutical formulation of the invention to said patient, contemporaneously with the patient's ingestion of a gluten-containing foodstuff.

In a third aspect, the present invention provides unit dose forms of the novel compositions of the invention. In various embodiments, the unit dose form can conveniently be used in the method of the invention. The dosage forms and pharmaceutical formulations of the invention can be used for the treatment of mammals as well as humans.

DETAILED DESCRIPTION OF THE INVENTION

In the current art of oral delivery (the administration of a substance by mouth, i.e., oral administration) of proteins, stabilization in the GI tract to prevent protein oxidation has not been discussed; instead, the focus of past efforts has been on the potential instability of the orally ingested protein to acid or to proteolysis by digestive enzymes. Thus, the need to provide additional stabilization of orally administered proteins to oxidation has not been appreciated prior to the present invention. Moreover, the benefits of such stabilization can be particularly beneficial, particularly for the oral delivery of enzymes to the stomach for the purpose of enhancing proteolysis. The present invention arose at least in part from the discovery that oxidation can play a key role in degradation of such orally administered enzymes.

The enzyme ALV001, a recombinant, modified form of the cysteine protease known as barley EPB2, was rapidly inactivated in ex vivo extracts of fed human gastric fluid and at rates that were significantly faster than observed at similar pH (3 to 5) and pepsin content. One aspect of the present invention arises from the discovery that the addition of antioxidants, particularly sulfur-containing antioxidants, such as sulfites or free thiols or agents that generate free thiols in gastric fluid, stabilize ALV001 (and thus, other cysteine proteases and cysteine-containing proteins) in gastric fluid. Surprisingly, these sulfur-containing antioxidants can also regenerate active enzyme from inactivated ALV001 in gastric fluid. Other antioxidants, such as ascorbic acid and methionine (in which the sulfhydryl group is methylated) did not stabilize (preserve the activity of) ALV001. ETDA did help stabilize ALV001 in ex vivo gastric fluid, albeit to a lesser extent than the antioxidants, and chelating agents generally therefore provide some stabilization, alone or in combination with an antioxidant, in accordance with the invention. Among the antioxidants, sodium sulfite and sodium metabisulfite are particularly effective in stabilizing ALV001.

As used herein, an "antioxidant" is a molecule capable of slowing or preventing the oxidation of other molecules. Oxidation is a chemical reaction that transfers electrons from a substance to an oxidizing agent. For use in the methods of the invention, physiologically acceptable antioxidants are of interest. Such antioxidants include, without limitation, reducing agents, ascorbic acid (vitamin C), lipoic acid, melatonin, uric acid, carotenes, retinols, tocopherols and tocotrienols, e.g. α-tocopherol (vitamin E), ubiquinone (coenzyme Q), and the like.

As used herein a "reducing agent" is any compound in the subclass of physiologically acceptable antioxidant compounds that reduces another species in a redox (reduction-oxidation) reaction and, in so doing, become oxidized and so serves as an electron donor in the redox reaction. Reducing agents for use in the formulations of the invention include, without limitation, methionine, glutathiol, dithiothreitol, dithioerythritol, β-mercaptoethanol, sodium metabisulfite, thioglycolate, cysteine, N-acetylcysteine, homocysteine, monothioglycerol, sodium sulfite, potassium bisulfite, sodium thiosulfite, and the like. Some such agents comprise a free thiol mercaptan) group, e.g. monothioglycerol, sodium thiosulfite, sodium metabisulfite, and the like. Agents that are in an oxidized form but that comprise a free thiol in acidic include, without limitation, α-lipoic acid, dithiothreitol, glutathione, and the like.

For certain antioxidants, the levels required to act in a one liter volume of the stomach would require an amount of antioxidant in the dosage form (or to be taken accompanying the dosage form) that are larger than currently accepted for toxicological reasons in the FDA's Inactive Ingredients Guide. Accordingly, their use in the compositions of the invention would likely require additional clinical testing of the antioxidant itself. In contrast, the sulfites and metabisulfites, especially their sodium and potassium salts and combinations, with their long history as preservatives in the food industry and their unusual potency as reducing agents for cysteine proteases as described herein are effective and accepted pharmaceutical excipients.

In some embodiments of the invention, the antioxidant is selected from sodium sulfite, sodium bisulfite, potassium bisulfate, potassium metabisulfite, sodium thiosulfate, glutathione, cysteine, homocysteine, sodium dithionite, thioglycerol, and acetylcysteine, alone or in combination. In other embodiments, a sulfur containing antioxidant is selected from the group consisting of sodium sulfite, sodium metabisulfite, N-acetylcysteine, homocysteine, cysteine, monothioglycerol, sodium thiosulfate, α-lipoic acid, and dithiothreitol. In some embodiments, the antioxidant is sodium metabisulfite.

The dosage of an antioxidant for purposes of the present invention may be empirically determined by assays known in the art, e.g. by testing a range of doses for stabilizing effect on a known concentration of protein. It will be understood by one of skill in the art that the dosage range will depend on the specific antioxidant. In some embodiments, the dosage of antioxidant is at least about 2 mg per dosage form; at least about 5 mg per dosage form; at least about 10 mg per dosage form, at least about 50 mg per dosage form; and not more than about 500 mg per dosage form, usually not more than about 300 mg per dosage form.

In some embodiments, the antioxidant is sodium metabisulfite, which may be present at a concentration of from about 2-50 mg per dosage form, preferably at from about 4-16 mg per dosage form, and most preferably at from about 6-10 mg per dosage form. In other embodiments, the antioxidant is cysteine, which may be present at a concentration of from about 5-400 mg per dosage form, preferably at from about 10-350 per dosage form, and most preferably at from about 50-300 mg per dosage form.

In various embodiments, the pharmaceutical formulation optionally comprises a chelating agent. The chelating agent is a physiologically acceptable component. Examples of the chelating agent include, without limitation, ethylenediaminetetraacetic acid (EDTA), sodium ethylenediaminetetraacetate, EGTA, phytic acid, citric acid, e.g. anhydrous citric acid, and the like. These can be used alone or in admixture. In one embodiment, the chelating agent is EDTA.

The dosage of a chelating agent may be empirically determined by assays known in the art, e.g. by testing a range of doses for stabilizing effect on a known concentration of protein, usually in combination with a selected antioxidant. It will be understood by one of skill in the art that the dosage range will depend on the specific chelating agent and protein to be administered. In some embodiments, the dosage is at least about 5 mg per dosage form; at least about 10 mg per dosage form; at least about 50 mg per dosage form, at least about 100 mg per dosage form; and not more than about 500 mg per dosage form, usually not more than about 300 mg per dosage form.

In some embodiments the chelating agent is citric acid, e.g. anhydrous citric acid, citric acid monohydrate, which may be present at a dose of from about 10 to about 500 mg per dosage form, usually at a dose of from about 25 to 350 mg per dosage form, and may be provided at a dose of from about 45-275 mg per dosage form.

In the formulations of the present invention, an antioxidant, e.g. a reducing agent as described above, is provided at a concentration effective to stabilize the protease active agent when exposed to gastric fluid, particularly when exposed to postprandial gastric fluid. The formulations are intended for in vivo use. However, for convenience, the stability may be tested in vitro, e.g. by combining the protease with postprandial gastric fluid and assessing proteolytic activity over a suitable period of time, e.g. for about 10 minutes, about 20 minutes, about 30 minutes, about 1 hour, or more. An effective concentration is sufficient to maintain at least about 25% of the enzyme starting activity, at least about 50% of the enzyme starting activity, at least about 75% of the enzyme starting activity, or at least about 90% of the enzyme starting activity, or is sufficient substantially to maintain the original activity for at least about 10 minutes, at least about 30 minutes, or longer.

Thus, the present invention provides novel formulations of proteins suitable for oral administration, which proteins are more resistant to oxidative degradation than currently available compositions. Those of skill in the art will appreciate that this discovery may enhance the therapeutic potential of a wide variety of proteins for oral administration, as prior testing or properties of a protein may have indicated that the protein would not provide therapeutic benefit on oral administration. For example, while papain is marketed as a nutraceutical, it has not found use as a therapeutic. Despite its high optimal temperature, papain may provide therapeutic benefit if administered in a formulation of the invention.

Those of skill in the art will therefore appreciate that the present invention provides pharmaceutical formulations of a protein suitable for oral administration that stabilize the protein in the fed stomach. In one embodiment, the protein is a protease. In one embodiment, the protease is a cysteine protease. In one embodiment, the formulation comprises, in addition to the protein, an antioxidant and/or a chelating agent. In one embodiment, the antioxidant is a sulfur-containing antioxidant. In various embodiments, the sulfur containing antioxidant is a sulfate, a free thiol, or an agent that generates a free thiol in gastric fluid.

Cysteine proteases have been reported to be useful for a variety of therapeutic purposes. For example, U.S. Pat. No. 6,241,973, incorporated herein by reference, describes cysteine proteases useful in teeth whitening. PCT Publication No. WO 2004/058816, incorporated herein by reference, describes cysteine proteases useful in vaccines against liver fluke. U.S. Patent App. Pub. No. 20080039400, incorporated herein by reference, describes cysteine proteases useful in treating inflammatory bowel disease and other conditions. U.S. Patent App. Pub. No. 20070264311, incorporated herein by reference, describes cysteine proteases useful in treating food intolerance. U.S. Patent App. Pub. No. 20070148267, incorporated herein by reference, describes cysteine proteases useful in regulating food intake. U.S. Patent App. Pub. Nos. 20060134017 and 20060134018, incorporated herein by reference, describe cysteine proteases useful in the prevention of bacterial adhesion to biological surfaces, i.e., for prevention of plaque formation. Cysteine proteases have also been described for systemic treatments, including, for example, induction of apoptosis in cancers. The compositions of the invention are accordingly useful in such methods.

In one embodiment, the cysteine protease is a protease capable of digesting a gluten peptide that is toxic to a Celiac sprue patient into non-toxic fragments, either alone or in combination with another protease. In one embodiment, the cysteine protease is barley endoprotease EPB2 or a modified form of that protease, or a recombinant version of either.

As used herein, a "pharmaceutical formulation", or "dosage form" includes any formulation intended for administration to humans or mammals and so includes not only formulations that undergo clinical testing and approval by regulatory authorities, such as the FDA, but also formulations that do not require regulatory approval, such as nutraceuticals.

Thus, for example, the compositions of the invention, including pharmaceutical formulations and dosage forms, can also include, depending on the formulation desired, pharmaceutically-acceptable, non-toxic carriers or diluents, which are defined as vehicles commonly used to formulate pharmaceutical compositions for animal or human administration. The diluent is selected so as not to adversely affect the biological activity of the protease. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The compositions of the invention can also include any of a variety of stabilizing agents, such as an antioxidant for example. The proteins or polypeptides in a composition of the invention can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

For oral administration, the active ingredient can be administered in solid dosage forms, such as capsules, tablets, and powders, such as in sachets or sprinkles, or in liquid dosage forms, such as elixirs, syrups, and suspensions. The active component(s) can be encapsulated in gelatin or hypromellose capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The components used to formulate the pharmaceutical compositions of the invention are preferably of high purity and are substantially free of potentially harmful contaminants (e.g., typically at least National Food (NF) grade, generally at least analytical grade, and more typically at least pharmaceutical grade). To the extent that a given compound must be synthesized prior to use, the resulting product is typically substantially free of any potentially toxic agents, particularly any endotoxins, which may be present during the synthesis or purification process.

Nutraceutical formulations are defined as "a food or part of a food that offers medical and/or health benefits including prevention or treatment of disease." (Dr. Stephen DeFelice, director of Foundation for Innovation In Medicine). Products range from isolated nutrients, dietary supplements and diets, to genetically engineered designer foods, functional foods, herbal products and processed foods such as cereal, soup and beverages. Functional foods, the most popular term among consumers but not a clearly delineated product category, are defined by Clare Hasler, Ph.D., of the University of Illinois, as foods that include "any modified food or food ingredients that may provide a health benefit beyond the traditional nutrients it contains." Nutraceutical formulations of interest include foods for veterinary or human use, such as health food bars, drinks and drink supplements, and the like. These foods are enhanced by the inclusion of a biologically active protease in a composition as provided herein.

When the dosage form or dosage forms are for treating celiac sprue and contain the enzyme ALV001, at least one dosage form may contain ALV001 alone or in combination with ALV002. The total content of ALV001 administered with a meal when ALV001 is administered without ALV002 is from 50 to 2000 mg of ALV001 protein, preferably between 100 and 1000 mg, and still more preferably between 100 and 600 mg of ALV001. When ALV001 and ALV002 are administered in a combination either in the same or separate dosage forms, they may be given in a ratio of 10:1 to 1:10, more preferably 3:1 to 1:3, and most preferably at a ratio of 1.5:1 to 1:1.5. If administered at approximately a 1:1 ratio, the total enzyme content given with a meal may be 50 to 2000 mg, more preferably 50 to 900 mg, and most preferably 100 to 400 mg.

The proteolytic activity of ALV001 at 25° C. against the chromogenic substrate Z-Phe-Arg-pNA is assessed by measuring the rate of change in the absorbance of light at 410 nm. The method is based on the release of para-nitroaniline (pNA, 4-nitroaniline) into solution, which absorbs light at 410 nm. The specification is ≥5000 u/mg for ALV001.

The proteolytic activity of ALV002 at 25° C. against the chromogenic substrate Z-Gly-Pro-pNA is assessed by measuring the rate of change in the absorbance of light at 410 nm. The method is based on the release of para-nitroaniline (pNA, 4-nitroaniline) into solution, which absorbs light at 410 nm. The specification is ≥3000 u/mg for ALV002.

In a second aspect, the present invention provides a method for preventing and/or treating Celiac sprue and/or dermatitis herpetiformis in a patient, said method comprising the step of orally administering a stabilized cysteine protease containing pharmaceutical formulation of the invention, wherein the formulation is stabilized with an antioxidant, and wherein the protease is capable of degrading gluten into fragments non-toxic to Celiac sprue patients upon oral administration, to said patient contemporaneously with the patient's ingestion of a gluten-containing foodstuff. U.S. Pat. Nos. 7,320,788 and 7,303,871 describe methods for identifying proteases capable of degrading gluten into fragments non-toxic to Celiac sprue patients.

In a third aspect, the present invention provides pharmaceutical formulations and dosage forms, i.e., unit dose forms, of the novel compositions of the invention. In various embodiments, the unit dose form can conveniently be used in the method of the invention.

EXAMPLES

1. Demonstration of Instability of ALV001 in Postprandial Human Gastric Fluid

Frozen human postprandial gastric fluids were thawed and centrifuged at 21,000 g for 5 minutes to pellet insoluble material, and the supernatant was used for this example. Between 50 and 200 µl of gastric fluid were added to the wells of a 96-well plate and incubated at 37° C. When antioxidants were added, they were added at this step. ALV001 or activated ALV001* (see PCT patent application No. 2008/003425, incorporated herein by reference, regarding how ALV001* (the active form of ALV001) is produced upon proteolytic cleavage of ALV001) was dissolved at a ratio of 20 µl water/mg powder, the concentration was measured by the absorbance at 280 nm, and the protein was added to the gastric fluid at a concentration of 0.1 to 0.3 mg/ml. At the specified sampling time, a 1.6 µl sample of gastric fluid was diluted in assay buffer to give a final volume of 280 µl, and the concentration was measured by a chromogenic activity assay using Z-Phe-Arg-p-nitroaniline (pNA) as the substrate. The method is based on the ability of pNA to absorb at 410 nm when released from the substrate. ALV001 is the proenzyme or zymogen for Endoprotease B (Isoform 2) that cleaves the C-terminal side of the arginine in the sequence Phe-Arg. Enzymatic cleavage and subsequent release of pNA may be monitored by the change in absorbance at 410 nm. To determine the reaction rate, the absorbance at 410 nm was measured every 10 seconds for 1 minute. The slope of the regression line divided by the enzyme concentration was the reported enzyme activity.

Stability of ALV001* in human gastric fluid was analyzed for 4 healthy volunteers fasting and at 15, 30, 45, 60, 75, and 90 minutes after eating a meal. The gastric fluid was withdrawn from these subjects through a nasogastric tube. The enzymatic activity of ALV001 was measured after 1.5, 5, 10, 20, and 60 minutes after addition to the gastric fluid. Western blots were also performed to investigate proteolytic degradation of ALV001* in the gastric fluid.

Figure 1:
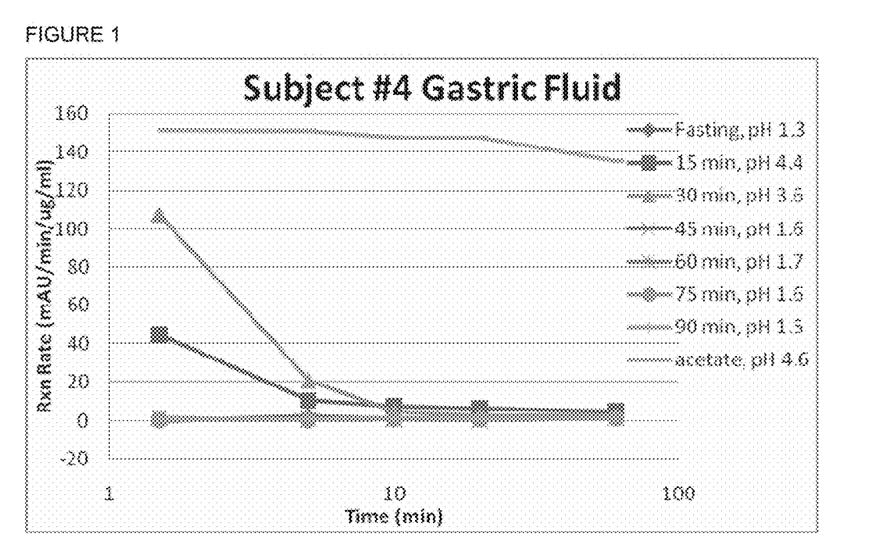
FIG. 1 shows the activity of ALV001*(the active form of the proenzyme ALV001) during incubation with postprandial gastric fluid.

FIG. 1 shows that ALV001* activity was only detectable in the 15 and 30 minute postprandial gastric fluid of Subject 4 and even then disappeared after 20 minutes of incubation. Similar results were observed for the other 3 subjects and with the addition of the zymogen, ALV001. In the fasting gastric fluid, rapid enzymatic degradation of ALV001* was expected due to low pH, for example, pH 1.3 for subject 4, and pepsin content. Postprandial gastric fluid has a transient increase in pH to the range of 3.5 or 4 or even greater, and at this greater pH, pepsin activity is reduced, and ALV001* is expected to be more resistant to proteolytic digestion and to degradation by acidity.

Figure 2:
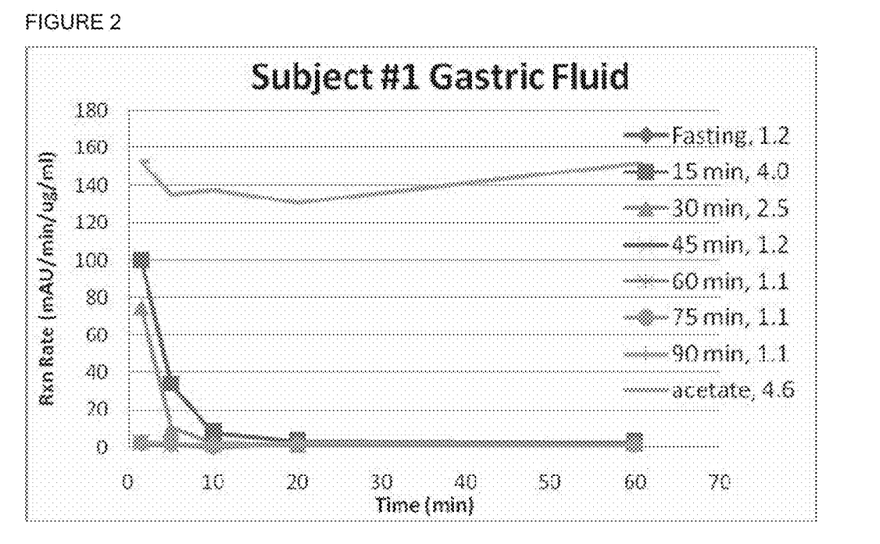
FIG. 2 shows the activity of ALV001 during incubation with postprandial gastric fluid.
Figure 3:
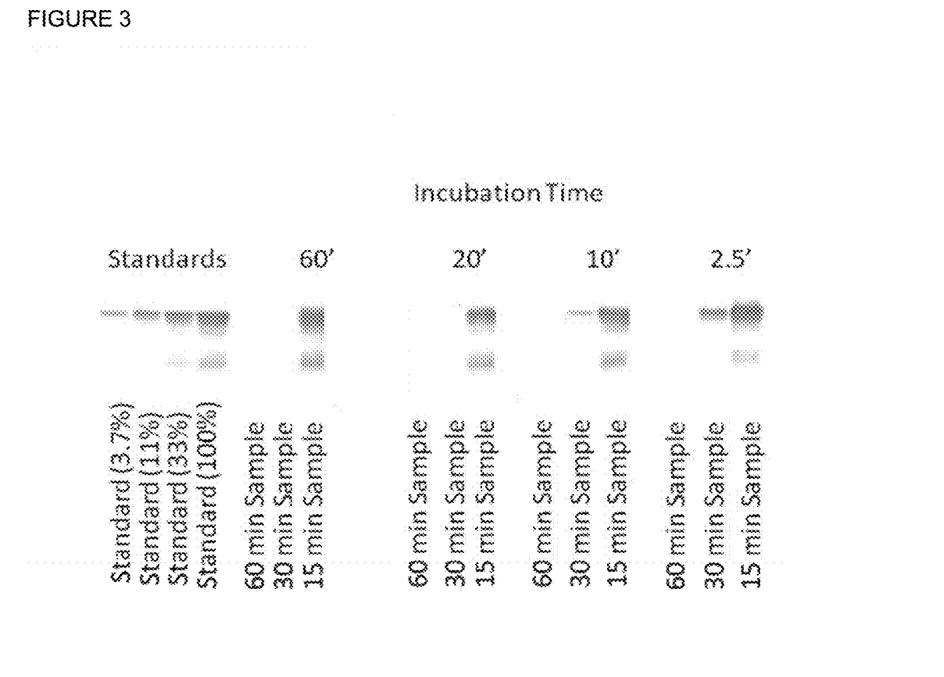
FIG. 3 is a western blot of ALV001 showing stabilization of ALV001 in postprandial gastric fluid with 1-thioglycerol.

As shown in FIG. 2, for subject 1 in the 15 minute postprandial sample at pH 4.0, the enzyme ALV001, was shown by the chromogenic assay to be rapidly inactivated, but the enzyme was still intact as measured by the Western blot, shown in FIG. 3. In the same subject, in the 30 and 60 minute postprandial gastric samples, which were pH 2.5 and 1.2, respectively, the enzyme was both inactive and proteolyzed. Similar data were obtained with the other patient samples. The conclusion was that an unexpected loss of enzymatic activity of this cysteine protease ALV001 in early postprandial gastric fluid samples resulted from a mechanism that was not related to proteolysis.

2. Demonstration of Stabilization of ALV001 in Postprandial Gastric Fluid by 1-Thioglycerol (Monothioglycerol)

Figure 4:
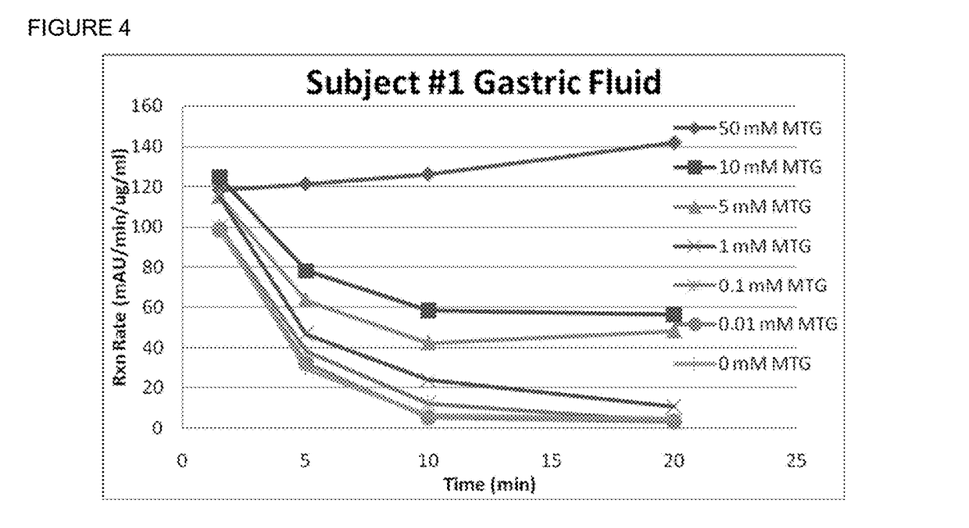
FIG. 4 shows the activity of ALV003 during incubation with postprandial gastric fluid in the absence or presence of 1-thioglycerol.

FIG. 4 shows the results of adding a range of concentrations of monothioglycerol (MTG), from 0.01 to 50 mM, to the wells of 15 minute postprandial gastric fluid as described above. A control without MTG was also included. The rate of loss of enzymatic activity of ALV001 decreased with increasing MTG concentrations with no loss at 50 mM MTG. Thus, the antioxidant MTG prevented the loss of enzyme activity of this cysteine protease.

Figure 5:
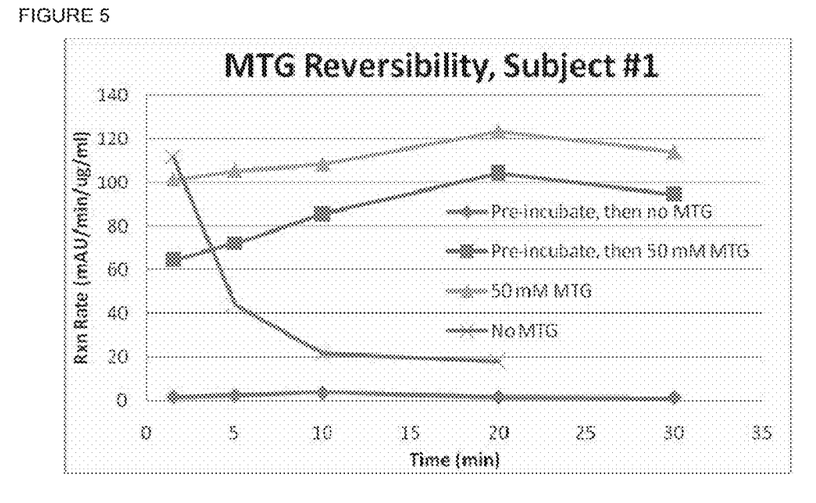
FIG. 5 shows the reversal of loss of enzyme activity with antioxidant.

Moreover, as shown in FIG. 5, pre-incubation of ALV003, a combination of ALV001 and ALV002 (a recombinant form of *Sphingomonas capsulata* prolyl endopeptidase) at approximately 1:1 enzyme ratio, in 15 minute postprandial gastric fluid followed by addition of 50 mM MTG versus no addition showed that the antioxidant MTG could reverse the loss of enzymatic activity of ALV001*. After approximately 20 minutes addition of MTG to nonfunctional pre-incubated ALV001*, nearly full enzymatic activity was restored.

3. Demonstration of Stabilization of ALV001 in Postprandial Gastric Fluid by Selected Reducing Agents Numerous reducing agents, in particular, N-acetylcysteine, L-cysteine, homocysteine, 2-mercaptoethanol, dithiothreitol, tris(2-Carboxyethyl) phosphine hydrochloride (TCEP), lipoic acid, sodium thiosulfate, sodium sulfite, and sodium metabisulfite, were all demonstrated to stabilize ALV001* in early postprandial gastric fluid. In contrast, L-methionine and ascorbic acid did not stabilize the enzyme. EDTA enhanced the stability of ALV001*, suggesting a dependency on metals for the inactivation.

Figure 6:
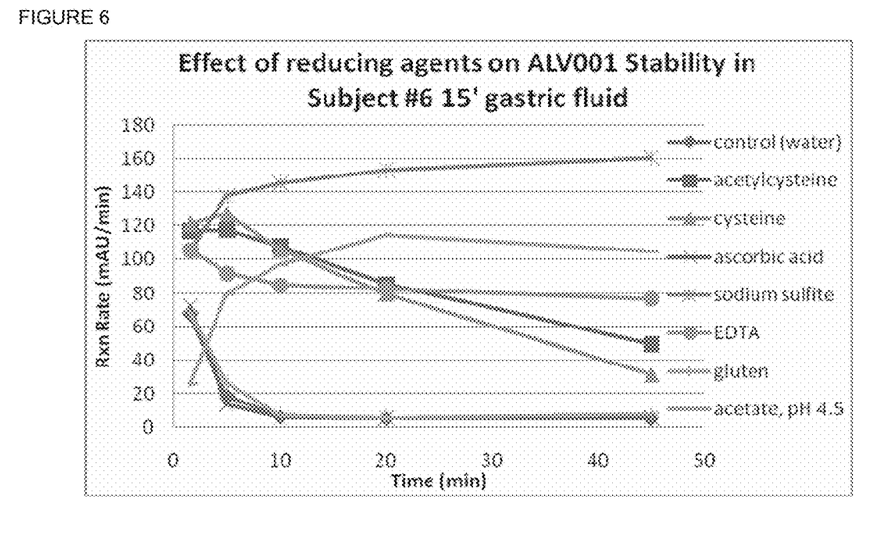
FIG. 6 shows the stabilization of ALV001 in postprandial gastric fluid with reducing agents.

Shown in FIG. 6, selected reducing agents were added at 5 mM to ex vivo postprandial gastric fluid that was obtained from a healthy volunteer 15 minutes after eating and was incubated at 37° C. The proenzyme ALV001 was added to the gastric fluid. Acetate buffer at pH 4.5 was used as a control, because ALV001 is fully activated under these conditions. Samples were taken to determine ALV001 activity after 1.5, 5, 10, 20, 45 minutes.

As can be seen from the figure, the cysteine protease ALV001 was fully active in acetate buffer. In contrast, the enzyme is rapidly inactivated in water, gluten, and even with ascorbic acid, an antioxidant, added. There is evidence of stabilization with the chelating agent, EDTA. Substantial improvements in stability were observed with the reducing agents, cysteine and N-acetylcysteine, and the most effective stabilization was demonstrated with the reducing agent sodium sulfite.

Figure 7:
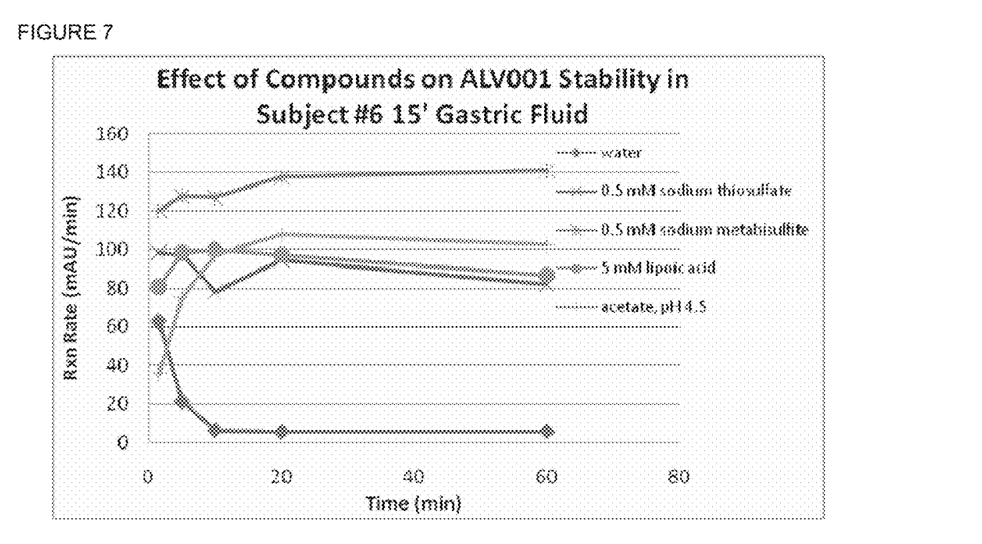
FIG. 7 shows stabilization as in FIG. 6, with sodium thiosulfate at 0.5 mM, sodium metabisulfite at 0.5 mM and lipoic acid at 5 mM.

Shown in FIG. 7, in a second set of tests performed in the same manner, sodium thiosulfate at 0.5 mM, sodium metabisulfite at 0.5 mM, and lipoic acid at 5 mM were demonstrated to improve the stability of ALV001 in postprandial gastric fluid.

Figure 8:
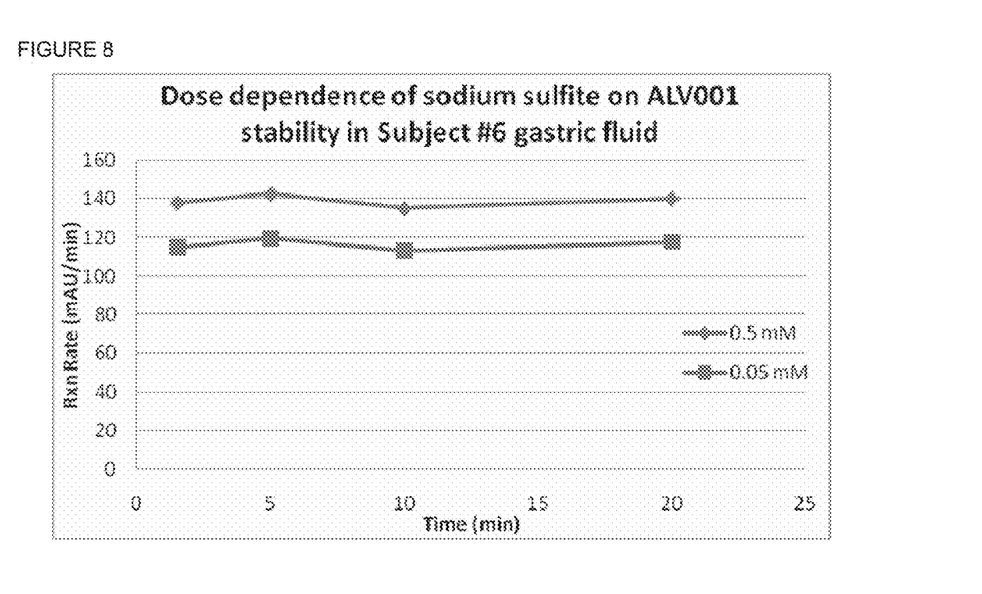
FIG. 8 shows a time course for stabilization with sodium sulfite.

Shown in FIG. 8, sodium sulfite was a particularly effective reducing agent to stabilize the ALV001, with the effective persisting down to 0.05 mM. Sodium metabisulfite improved stability of ALV001 even at concentrations of 50 µM.

Figure 9:
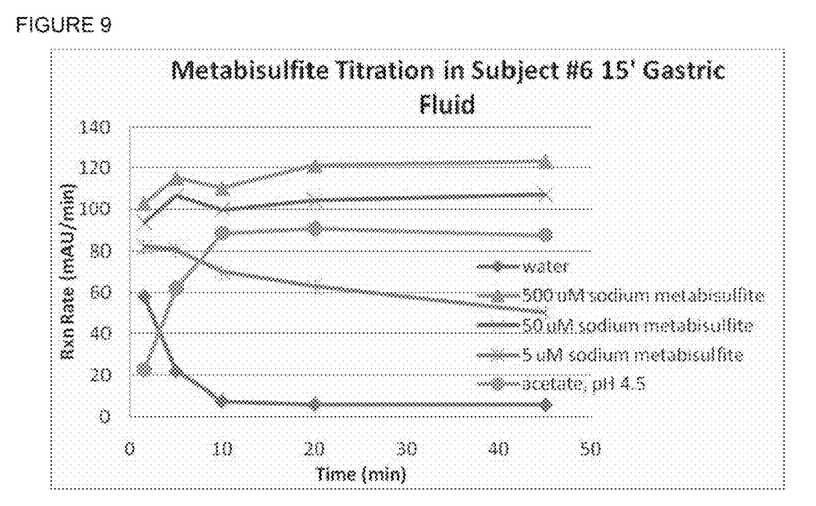
FIG. 9 shows a titration of sodium metabisulfite.
Figure 10:
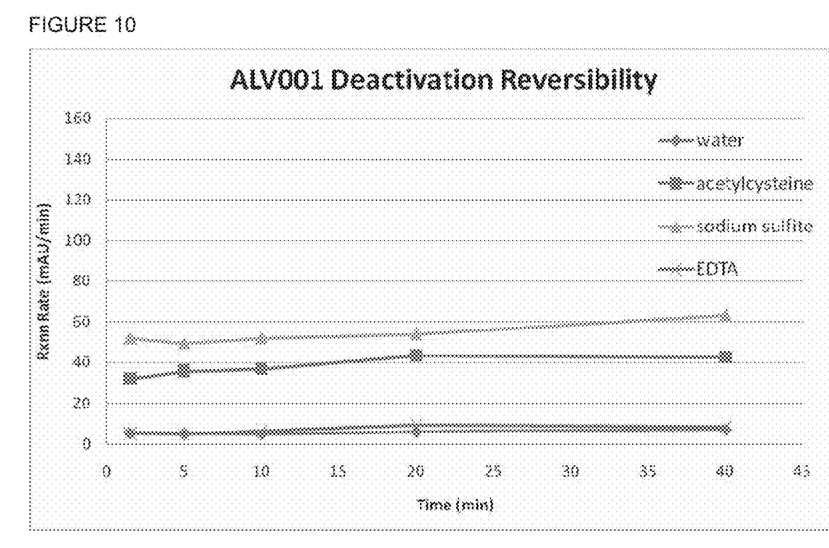
FIG. 10 shows a restoration of activity after the addition of reducing agents.

Shown in FIG. 9, in another set of tests, the ability of these reducing agents and a chelating agent to reverse the degradation of ALV001 in gastric fluid was examined. ALV001 was added to postprandial gastric fluid and incubated for 15 minutes at 37° C. Reducing agents were added at 5 mM to the gastric fluid and then samples were taken to examine ALV001 activity at 1.5, 5, 10, 20, and 40 minutes after the addition of the reducing agents. The buffer control and EDTA did not restore the enzyme activity, and sodium sulfite and acetylcysteine partially restored the enzyme activity.

Figure 11:
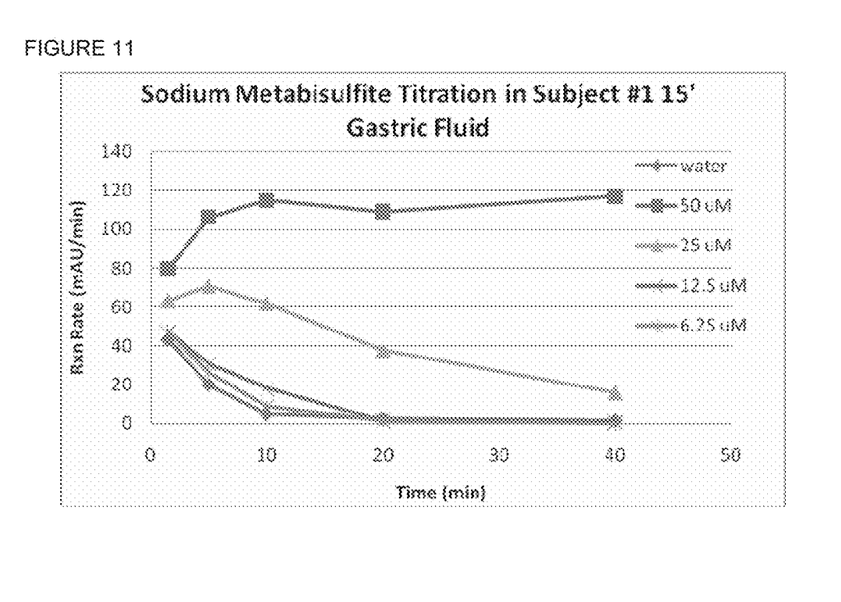
FIG. 11 shows a dose dependence of sodium metabisulfite in stabilization of ALV001.
Figure 12:
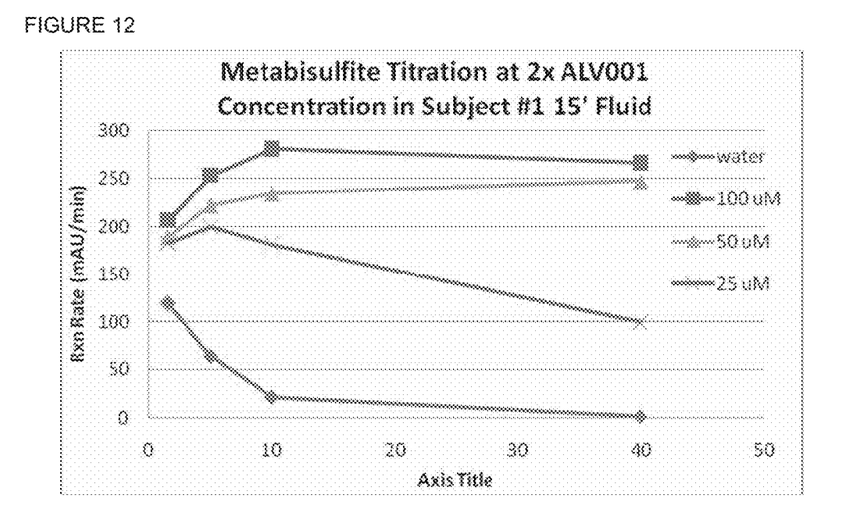
FIG. 12 shows a metabisulfite titration at 2× ALV001 enzyme concentration.

Shown in FIG. 11, the dose dependence of sodium metabisulfite and improved stability of ALV001 at 0.12 mg/ml was measured in postprandial gastric fluid. Samples were taken at 1.5, 5, 10, 20, and 40 minutes. While sodium metabisulfite provided considerable stabilization even at 25 µM, the best stabilization was observed at 50 µM. This test was repeated at twice the enzyme concentration to ensure that the effect was not dependent on enzyme concentration, FIG. 12.

4. Dosage Form Stability Testing 65 mg of ALV003, a mixture consisting of 38 mg ALV001 (Lot A031207) and 27 mg of ALV002 (Lot B061707) were weighed into each hypromellose capsules size 0 (Qualicaps). For one set of capsules 0.8 mg per capsule sodium metabisulfite (Spectrum, Lot WG 0855) was first added to the ALV003 powder and it was mixed by hand with a spatula before placing in the capsules. The hypromellose capsules were placed in 30 ml polypropylene vials with 1 g desiccant canisters (Sorb-it). The vials were transferred into 25° C./60% RH and 40° C./75% RH stability chambers. Samples were withdrawn at Initial (T=0), 2, 4, and 8 week intervals for enzyme activity analysis.

5. Sodium Metabisulfite in Grape Juice as Antioxidant

The compositions of the invention include foodstuffs modified to contain a therapeutic protease and an antioxidant, reducing agent, and/or chelating agent. This example illustrates the use of the reducing agent sodium metabisulfite in combination with the cysteine protease ALV001 taken or admixed with grape and other juices. To demonstrate the ability to stabilize ALV001 in gastric fluid by grape juice, as an example, the following experiment was performed. ALV001 was prepared in water at 20 µl/mg powder or approximately 9.5 mg/ml. Into a 96 well plate was added 54 µl 15 minute postprandial gastric fluid pre-incubated to 37° C., 5 µl of juice and 2.66 µl of ALV001 diluted 1:1 with water. The juices tested were sparkling white grape juice (Welch's), white grape juice (Welch's), white grape juice (Safeway), lime juice (Realime), and lemon juice (Safeway). These fruit juices contain metabisulfite as a preservative. Water was used as a control. The water control showed the usual rapid degradation of ALV001 in postprandial gastric fluid. The lime and lemon juice showed slower degradation of ALV001, and all 3 grape juices were stable over the 20 minute time course of the test.

Thus, in one embodiment of the invention, ALV003 or another glutenase is administered (for example, 300 mg of drug) in an HPMC capsule and is taken with a glass, approximately 100 to 250 ml or more, of grape juice.

Figure 13:
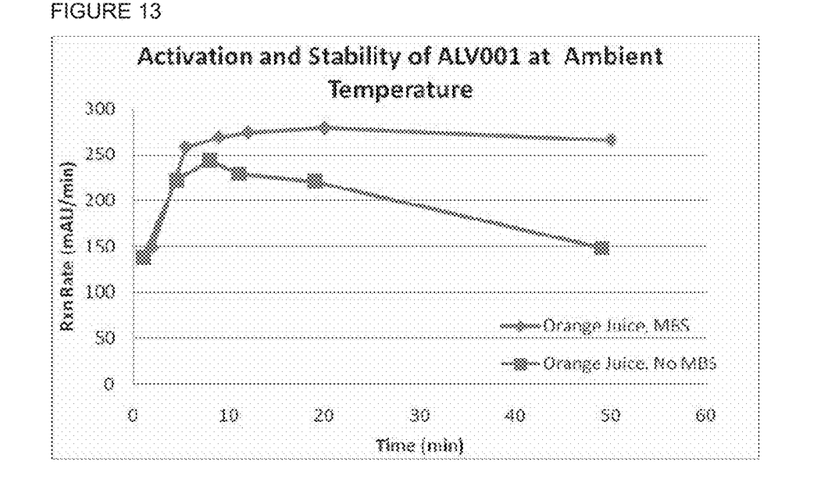
FIG. 13 shows that sodium metabisulfite stabilizes ALV001 activity in orange juice. 3 mg/ml ALV001 was reconstituted in orange juice with or without 840 μM sodium metabisulfite. Chromogenic enzyme activity was measured at the indicated timepoints to determine the relative amount of functional enzyme.

6. Sodium Metabisulfite in Orange Juice as Antioxidant 3 mg/ml ALV001 was reconstituted in orange juice with or without 840 µM sodium metabisulfite. Chromogenic enzyme activity was measured as described above, at the indicated timepoints, to determine the relative amount of functional enzyme, as shown in FIG. 13. The data show increased stability in the presence of sodium metabisulfite.

7. Cysteine as Antioxidant

Figure 14:
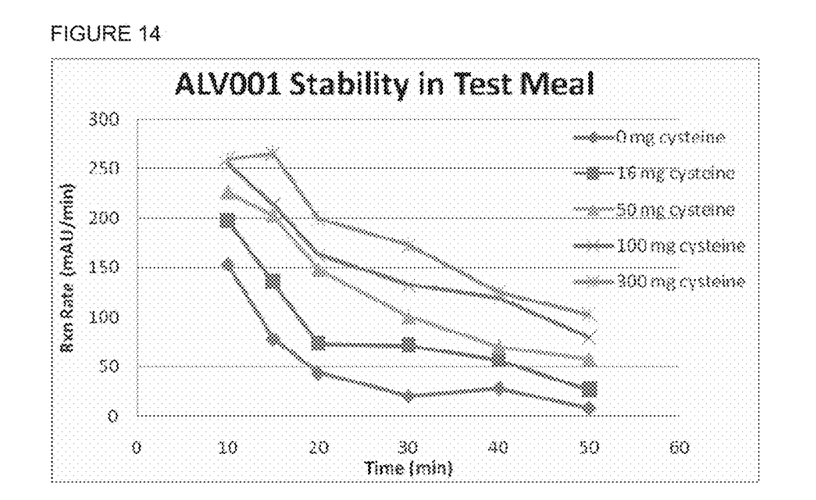
FIG. 14 shows that cysteine stabilizes ALV001 activity under simulated postprandial gastric conditions. A gluten-free meal was chewed and spit into resting gastric fluid. ALV003 and varying levels of cysteine were added at time 0 and the stability of ALV001 activity was tested by monitoring chromogenic enzyme activity over time. Gastric acid secretion was simulated throughout the experiment.

A gluten-free meal was chewed and spit into resting gastric fluid. ALV003 and varying levels of cysteine were added at time 0, and the stability of ALV001 activity was measured by monitoring chromogenic enzyme activity over time. Gastric acid secretion was simulated throughout the experiment. As shown in FIG. 14, cysteine stabilizes ALV001 activity under these simulated postprandial gastric conditions.

Figure 15:
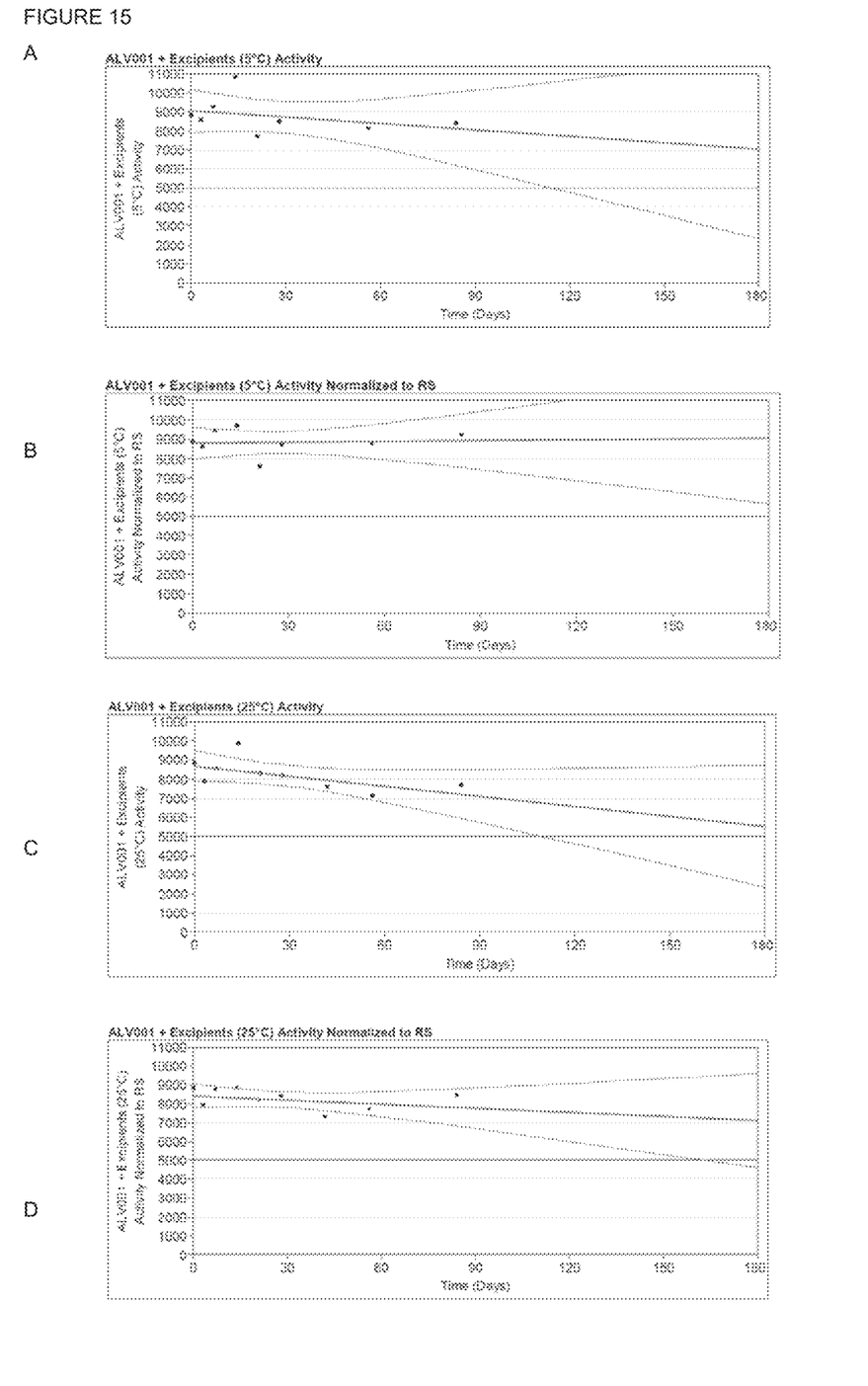
FIG. 15 shows that ALV001 stability study. 150 mg of enzyme was formulated with 300 mg. citric acid monohydrate, and 8 mg. sodium bisulfite, placed in polypropylene bottle, and sealed in foil pouches. A chromogenic assay was measured at specified time points to assess stability.

8. Citric Acid Monohydrate and Sodium Bisulfite as Antioxidant 150 mg of enzyme (ALV001) was formulated with 300 mg. citric acid monohydrate, and 8 mg. sodium metabisulfite, placed in polypropylene bottle, and sealed in foil pouches. A chromogenic assay was measured at specified time points to assess stability, as shown in FIG. 15.

9. Dosage Forms

The present invention provides a dosage form that contains 300 mg or 900 mg ALV003, optionally in a tablet form, with added mannitol and microcrystalline cellulose and 8 mg sodium metabisulfite.

The present invention provides a dosage form that contains a lyophilized powder of ALV001 in which sodium metabisulfite had been added to the solution prior to lyophilization instead of monothioglycerol at a ratio from 100:8 (w/w) to a ratio of 900:4 (w/w).

The present invention provides a dosage form that contains a spray dried powder of ALV001 in which sodium metabisulfite had been added to the solution prior to spray drying instead of monothioglycerol at a ratio from 100:8 (w/w) to a ratio of 900:4 (w/w).

The present invention provides a dosage form that contains immediate release ALV001 in a range of 100 to 900 mg and sodium metabisulfite in a range of 1 to 10 mg.

The present invention provides a dosage form that contains controlled release ALV001 in a range of 100 to 900 mg and sodium metabisulfite in a range of 1 to 10 mg released from 30 minutes to 6 hours.

The present invention provides a dosage form that contains controlled release ALV001 in a range of 100 to 900 mg and sodium metabisulfite in a range of 1 to 10 mg released from 30 minutes to 6 hours.

The present invention provides a dosage form that contains pulsed release ALV001 in a range of 100 to 900 mg and sodium metabisulfite in a range of 1 to 10 mg in an immediate release pulse and a second pulse released from 20 minutes to 6 hours later.

The present invention provides a dosage form that contains a protease and a quantity of an antioxidant that achieves an antioxidant concentration of at least 30, 50, 100, or 200 µM in the stomach.

The present invention provides a dosage form that contains a protease and a quantity of a compound that generates a concentration of free thiol of at least 100, 200, or 500 µM in the stomach.

The present invention provides a dosage form that contains sodium metabisulfite and may contain both ALV001 and ALV002 where one enzyme component is formulated to provide an immediate release and the other enzyme component is either a pulsed release or to provide a controlled release.

All of the ALV001 dosage forms above can also be modified to include a second protease. In one embodiment, the second protease is a prolyl endopeptidase (PEP). In one embodiment the PEP is *Sphingomonas capsulata* PEP, for example and without limitation, as described in PCT Pub. No. 2008/115411. In various embodiments, between 1-2000 mg of the PEP and ALV001 are dosed at a PEP:ALV001 weight ratio of between 1:100 to 100:1, more preferably between 1:20 to 20:1, more preferably between 1:5 and 5:1, and most preferably at a 1:1 ratio. In one embodiment, the dosage form is constructed so that the ALV001 and antioxidant, e.g., sodium metabisulfite, are immediately released, and the PEP is released either immediately; or is released in one or more short, delayed pulses (from 10 minutes to 3 hours); or is released in sustained release over 10 minutes to 3 hours.

In one embodiment, the present invention provides a dosage form in which the antioxidant is an antioxidant other than sodium metabisulfite.

The present invention provides oral dosage forms comprising a protein and an antioxidant selected from the group consisting of sodium sulfite, sodium bisulfite, potassium bisulfate, potassium metabisulfite, alone or combination; sodium thiosulfate; glutathione, cysteine, homocysteine, sodium dithionite, thioglycerol; and acetylcysteine.

The present invention may provide roller compacted granules or pellets of the enzyme.

The antioxidant may be either contained in the granules or pellets or blended with the granules or pellets and either filled or compressed into a dosage form.

The pharmaceutical formulations of the invention can be in the form of, for example and without limitation, particles, particles in capsule or sachet, or tablet. Tablets may be single layer, bilayer, or multilayer and may be coated or uncoated. The formulation can, for example and without limitation, be added to a food or drink and then administered, for example, as a sprinkled powder or granule formulation or as a spread in the form of a jam or powder. A capsule of low water content may be desired for stability, and hypromellose capsules, HPMC, of size 1, 0, or 00, can be used. Capsules can be packaged in a dry environment either with desiccant or desiccant packs or if in blisters under dry nitrogen or other dry environment.

The pharmaceutical formulations of the invention can comprise a lubricant such as magnesium stearate, stearic acid, sodium stearyl fumarate, or sodium stearyl lactylate, hydrogenated vegetable oil (such as hydrogenated and refined triglycerides of stearic and palmitic acids). These may be at 0.3 to 5% of weight of the dosage form. If mannitol is contained at a high concentration in the lyophilized, then higher concentrations of lubricant may be used.

The cysteine protease (or other protein active pharmaceutical ingredient) powder may be blended with lubricant or other excipients such as a filler or binder and granulated. If the cysteine protease is unstable with water and temperature, then these can be roller compacted into granules, if necessary using chilled rollers for stability. One may optionally include an agent that modifies or controls pH, at least for the first few minutes after the dosage form is in the GI tract, to facilitate activation of zymogen proteins such as ALV001.

Fillers such as dicalcium phosphate, microcrystalline cellulose, maltodextrins, mannitol, lactose, sucrose, or trehalose may be included and blended with the powders or included in the lyophilized powder or spray-dried powder. More hydrophilic fillers such as microcrystalline cellulose may be avoided for certain enzymes, such as ALV001.

Controlled-release excipients may be blended in to form polymeric drug-containing matrices. These matrices may be from about 1 mm in diameter to the size of a full tablet 10 to 12 mm in width and even 1.8 cm or more in length. These matrices can provide extended-release into the stomach being retained with food for % to 8 hours depending on the size. These matrices may or may not be swellable. If swellable, extended-release hydrophilic polymers that are appropriate include cellulose polymers and their derivatives (such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, poly (2-ethyl-2-oxazoline), poly(ethyleneimine), polyurethane hydrogels, and crosslinked polyacrylic acids and their derivatives. Further examples are copolymers of the polymers listed in the preceding sentence, including block copolymers and grafted polymers. Extended-release coatings could also be prepared on these particles using some of the above polymers.

The invention claimed is:

1. A solid pharmaceutical formulation in the form of a capsule; a powder, sprinkle or particles in a capsule or sachet; or a tablet of barley endoproteinase B2 (EPB2) or a recombinant form of barley EPB2 for oral administration in unit dose form that contains from about 5 to 400 mg of cysteine and from 50 to 2000 mg of said barley EPB2.

2. The pharmaceutical formulation of claim 1, further comprising a chelator.

3. The pharmaceutical formulation of claim 2, wherein the chelator is ethylenediaminetetraacetic acid (EDTA) or citric acid.

4. The pharmaceutical formulation of claim 3, wherein the chelator is present in a dosage of at least about 5 mg per dosage form to not more than about 500 mg per dosage form.

5. A method for treating Celiac sprue and/or dermatitis herpetiformis in a patient, said method comprising the step of orally administering a therapeutically effective amount of the pharmaceutical formulation of claim 1, either alone or in combination with another protease, to said patient contemporaneously with the patient's ingestion of a gluten-containing foodstuff.

6. The pharmaceutical formulation of claim 4, wherein said chelator is citric acid, which is present at about 10-300 mg per dosage form.

7. The pharmaceutical formulation of claim 6, wherein said chelator is citric acid, which is present at about 30-200 mg per dosage form.

\* \* \* \* \*